(12) United States Patent
Alsters et al.

(10) Patent No.: US 6,593,494 B2
(45) Date of Patent: Jul. 15, 2003

(54) PROCESS FOR PREPARING CARBOXYLIC ACIDS BY OXIDATION OF ALDEHYDES

(75) Inventors: Paul Alsters, Maastricht (NL); Elisabeth Schmieder Van De Vondervoort, Haelen (NL)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 0 days.

(21) Appl. No.: 10/107,429

(22) Filed: Mar. 28, 2002

(65) Prior Publication Data

US 2002/0143206 A1 Oct. 3, 2002

(30) Foreign Application Priority Data

Mar. 29, 2001 (AT) .............................................. 506/01

(51) Int. Cl.$^7$ .......................... C07C 51/235; C07C 51/23
(52) U.S. Cl. ........................................ 562/531; 562/418
(58) Field of Search .................................. 562/418, 531

(56) References Cited

U.S. PATENT DOCUMENTS

| | | | | |
|---|---|---|---|---|
| 3,114,769 A | * | 12/1963 | Barone et al. ............... | 562/533 |
| 3,965,163 A | * | 6/1976 | Oda et al. ................... | 562/534 |
| 4,225,694 A | | 9/1980 | Dalton, Jr. et al. | |
| 4,259,211 A | * | 3/1981 | Krabetz et al. ............. | 252/443 |
| 4,322,435 A | * | 3/1982 | Kojima et al. ............... | 424/305 |
| 4,341,900 A | * | 7/1982 | Ishii et al. ................... | 562/532 |
| 4,365,087 A | * | 12/1982 | Kadowaki et al. .......... | 562/534 |
| 4,435,598 A | * | 3/1984 | Hinnekamp .................. | 562/546 |
| 5,264,625 A | * | 11/1993 | Hammon et al. ........... | 562/532 |

FOREIGN PATENT DOCUMENTS

WO         99/52850         10/1999

OTHER PUBLICATIONS

Patent Abstracts of Japan, vol. 6, No. 122 (C–122), Jul. 7, 1982—Abstract of JP 57–48931.
Kanade et al., Indian Journal of Chemistry, vol. 30B, pp. 984–985, Oct. 1991.
Swarnalakshmi et al., Indian Journal of Chemistry, vol. 23A, pp. 386–388, May 1984.

* cited by examiner

*Primary Examiner*—Alan L. Rotman
*Assistant Examiner*—Taylor Victor Oh
(74) *Attorney, Agent, or Firm*—Wenderoth, Lind & Ponack, L.L.P.

(57) ABSTRACT

Process for the oxidation of aldehydes to the corresponding acids in which an aldehyde as substrate is oxidized to the corresponding acid in the presence of an equimolar amount, or a molar excess, of periodate, catalytic amounts of dichromate or $CrO_3$, and in the presence of an acid in water, a water/solvent mixture or in a solvent at a temperature of −20° C. to +50° C.

7 Claims, No Drawings

PROCESS FOR PREPARING CARBOXYLIC ACIDS BY OXIDATION OF ALDEHYDES

The invention relates to a process for the oxidation of aldehydes to the corresponding carboxylic acids.

Oxidation is a fundamental transformation in organic synthesis, so that numerous methods have already been described for it in the literature. Despite this, direct conversion of aldehydes to the corresponding carboxylic acids, in particular in the presence of labile substituents, for example an unsubstituted or substituted benzyl group, is still associated with problems. Conventional methods, which use permanganate (Org. Syn., Coll. Vol. 2, 538 (1943)) or chromium-based reagents (J. Org. Chem., 2868 (1967)), only lead to moderate yields of the desired carboxylic acid. More recent methods which are based, for example, on the use of hypochlorite (Tetrahedron Lett., 23, 3131 (1982)) or $RuCl_3/NaIO_4$ (J. Org. Chem., 46, 3936 (1981)) are similarly without success. These variants, in addition to the low yields, also have the disadvantage that extreme overoxidation with breakage of the C—C bond readily occurs, so that novel oxidation methods are still being sought.

It is an object of the invention to find a suitable method for the oxidation of aldehydes to the corresponding carboxylic acids in which, in particular, even the reaction of highly enolizable aldehydes in the presence of labile substituents is ensured to a great extent.

Unexpectedly, this object was achieved by using periodate in combination with dichromate or $CrO_3$ in the presence of an acid.

The invention therefore relates to a process for the oxidation of aldehydes to the corresponding acids, which comprises oxidizing an aldehyde as substrate to the corresponding acid in the presence of an equimolar amount, or a molar excess, of periodate, catalytic amounts of dichromate or $CrO_3$, and in the presence of an acid in water, a water/solvent mixture or in a solvent at a temperature of from $-20°$ C. to $+50°$ C.

In the inventive process, aldehydes are oxidized to the corresponding acids.

Suitable aldehydes are compounds of the formula I

where R is an unbranched, branched or cyclic, unsubstituted or substituted $C_1$–$C_{20}$ alkyl radical, an aryl or heteroaryl radical or a heterocycle.

Alkyl radicals are taken to mean unbranched, branched or cyclic alkyl groups. These radicals can be unsubstituted or substituted by one or more substituents which are inert under the reaction conditions, such as acyl, carboxyl, halogen, $C_1$–$C_8$-alkoxy, $C_3$–$C_8$-cycloalkyl, unsubstituted or substituted aryl radical, such as phenyl or naphthyl, heteroaryl, heterocycle etc., each of which may be substituted by phenyl, $C_1$–$C_{12}$-alkyl, $C_1$–$C_8$-alkoxy, halogen, aryloxy.

Aryl is taken to mean phenyl or naphthyl which in turn can be unsubstituted or substituted by acyl, carboxyl, halogen, $C_1$–$C_8$-alkoxy, $C_3$–$C_8$-cycloalkyl, etc.

Heteroaryl radicals are 5- or 6-membered aromatic rings which have 1 to 3 heteroatoms selected from the group consisting of O, N or S. These radicals can also be unsubstituted or substituted by acyl, carboxyl, halogen, $C_1$–$C_8$-alkoxy, $C_3$–$C_8$-cycloalkyl, etc. In addition, the heteroaryl radicals can be present as benzocondensed ring systems which can also be substituted as described above.

Heterocyclic radicals are 5- or 6-membered nonaromatic rings which have 1 to 3 heteroatoms selected from the group consisting of O, N or S. These radicals can in turn be unsubstituted or substituted by acyl, carboxyl, halogen, $C_1$–$C_8$-alkoxy, $C_3$–$C_8$-cycloalkyl, etc. In addition, the heterocyclic radicals can also be present as benzocondensed ring systems which can also be substituted as described above.

Preferred aldehydes are aldehydes of the formula I where R is an unbranched or branched, unsubstituted or substituted $C_1$–$C_{20}$ alkyl radial. Preferred substituents are halogen, $C_1$–$C_8$-alkoxy, aryloxy or phenyl which is unsubstituted or substituted by $C_1$–$C_{12}$-alkyl, halogen, $C_1$–$C_8$-alkoxy, aryloxy.

Particular preference is given to aldehydes of the formula I where R is an unbranched or branched $C_1$–$C_2$-alkyl radical which is substituted by a phenyl which is monosubstituted or disubstituted by $C_1$–$C_4$-alkyl, $C_1$–$C_4$-alkoxy, phenoxy, fluorine or chlorine.

The inventive oxidation of aldehydes is performed in the presence of an equimolar amount, or of a molar excess, of periodate. Preferably, 1.1 to 10 molar equivalents, particularly preferably 1.2 to 5 molar equivalents, of periodate are used. Periodate is used here as Na, K or $Bu_4N$ salt, sodium periodate being preferred.

In addition, for the inventive oxidation, dichromate or $CrO_3$ is used in catalytic amounts. Suitable dichromates are Na dichromate or K dichromate. Preferably sodium dichromate is used. The amount of dichromate or $CrO_3$ is from about 0.1 to 20 mol %, based on the substrate. Preferably, an amount of from 0.3 to 3 mol % dichromate or $CrO_3$ is added.

As third component an acid is added. Suitable acids here are sulfuric acid, HCl, $HNO_3$, p-toluenesulfonic acid (p-TSA), $HBF_4$, $H_5IO_6$, $CF_3SO_3H$ or perfluorotetradecanoic acid (PFTDA) or mixtures thereof. Preferred acids are $H_2SO_4$, $HNO_3$ and $H_5IO_6$, and mixtures thereof.

The acid is used in an amount corresponding to 1–30 mol % $H^+$, preferably 5–20 mol % $H^+$, based on the substrate.

The inventive oxidation is performed in water, in a solvent or in a water/solvent mixture.

Suitable solvents are toluene, chloroform, dichloromethane, ethyl acetate, diethyl ether, methyl t-butyl ether, dimethoxyethane, 2-methoxyethyl ether, triethylene glycol dimethyl ether, dioxane, THF, acetone, isopropyl acetate and acetonitrile.

In the oxidation of the aldehydes, preferably, the three oxidation components periodate, dichromate or $CrO_3$, and acid are dissolved in water. The substrate to be oxidized is then added with stirring. The substrate can be added as such or if appropriate as solution in one of the above described solvents or water/solvent mixture.

The reaction temperature, depending on the solvent system chosen, is from $-20°$ C. to $+50°$ C., preferably from $-10°$ C. to $+30°$ C., and particularly preferably from $0°$ C. to $25°$ C.

If a two-phase system is employed, the reaction mixture is stirred vigorously during the entire reaction. If only an aqueous phase is employed, the intensive stirring may not be necessary.

The reaction time depends on the substrate used and is between 1 and 40 hours. Preferably, the reaction time is between 6 and 30 hours, particularly preferably between 12 and 25 hours.

If appropriate, a further portion of periodate and/or acid can be added to the reaction mixture after a part of the reaction time, in order to complete the oxidation to the carboxylic acid.

At the end of the oxidation the corresponding carboxylic acid is isolated from the reaction mixture. Depending on the physical state, this is performed by conventional methods, for example by extraction, filtration etc.

The remaining reaction solution can be worked up to regenerate the periodate. This can be performed by methods known from the literature, for example by chemical or electrochemical oxidation. Preferably the periodate is regenerated by ozone, as described for example, in WO 98/27118. The regenerated periodate can then be reused for further oxidations.

By means of the inventive process, aldehydes are up to 70% or more converted to the corresponding carboxylic acids, depending on the reaction time. Unreacted aldehydes may be readily removed from the end product when it is isolated.

A further advantage of the process is the simple reaction procedure, where it is an advantage, in particular, that even in the case of aldehydes having labile constituents, for instance an unsubstituted or substituted benzyl group, high yields and high purities are obtained, compared with the prior art.

EXAMPLE 1

P-methoxyphenylacetic Acid 1.44 equivalents (7.7 g) of sodium periodate $NaIO_4$, 0.6 mol % (0.045 g) of sodium dichromate $Na_2Cr_2O_7 \cdot 2H_2O$ and 3 g of 1N sulfuric acid $H_2SO_4$ (12 mol %) were dissolved in 50 ml of water. To this solution were added 25 mmol (3.75 g) of 4-methoxyphenylacetaldehyde and 25 ml of toluene, whereupon the reaction mixture was stirred for 17 h at 20° C. The phases were then separated and the aqueous phase was extracted with 2×10 ml of toluene. 30 ml of 1N NaOH were added to the combined toluene phases. The basic water phase was made acidic with 3 g of conc. $H_2SO_4$ and extracted with 2×25 ml of toluene. The combined organic phases were washed 3× with $H_2O$, dried over $Na_2SO_4$ and evaporated to dryness. 17 mmol (2.82 g) of p-methoxyphenylacetic acid (yield 68% of theory) with a purity of 98% were obtained.

What is claimed is:

1. A process for the oxidation of aldehydes of the formula I

(I)

where R is an unbranched, branched or cyclic, unsubstituted or substituted $C_1$–$C_{20}$-alkyl radical, an aryl radical to the corresponding acids, which comprises oxidizing the aldehyde, as a substrate, to the corresponding acid in the presence of an equimolar amount, or a molar excess, of periodate, catalytic amounts of dichromate or $CrO_3$, and in the presence of an acid selected from the group consisting of sulfuric acid, HCl, $HNO_3$, p-toluenesulfonic acid, $HBF_4$, $H_5IO_6$, $CF_3SO_3H$ or perfluorotetradecanoic acid or mixtures thereof, in water, a water/solvent mixture or in a solvent, the solvent being selected from the group consisting of toluene, chloroform, dichloromethane, ethyl acetate, diethyl ether, methyl t-butyl ether, dimethoxyethane, 2-methoxyethyl ether, triethylene glycol dimethyl ether, dioxane, THF, acetone, isopropyl acetate and acetonitrile, at a temperature of from −20° C. to +50° C.

2. The process as claimed in claim 1, wherein the aldehydes are compounds of the formula I where R is an unbranched or branched $C_1$–$C_{20}$-alkyl radical which is unsubstituted or substituted by halogen, $C_1$–$C_8$-alkoxy, aryloxy or phenyl which is unsubstituted or substituted with $C_1$–$C_{12}$-alkyl, halogen, $C_1$–$C_8$-alkoxy or aryloxy.

3. The process as claimed in claim 1, wherein the aldehydes are compounds of the formula I where R is an unbranched or branched $C_1$–$C_2$-alkyl radical which is substituted by a phenyl which is monosubstituted or disubstituted by $C_1$–$C_4$-alkyl, $C_1$–$C_4$-alkoxy, phenoxy, fluorine or chlorine.

4. The process as claimed in claim 1, wherein from 1.1 to 10 molar equivalents of periodate are added.

5. The process as claimed in claim 1, wherein periodate is used in the form of the Na, K or $Bu_4N$ salt.

6. The process as claimed in claim 1, wherein dichromate or $CrO_3$ is added in amounts of from 0.1 to 20 mol % based on the aldehyde.

7. The process as claimed in claim 1, wherein an amount of acid corresponding to 1–30 mol % $H^+$, based on the substrate is used.

* * * * *